US009612181B2

(12) United States Patent
Mann et al.

(10) Patent No.: US 9,612,181 B2
(45) Date of Patent: Apr. 4, 2017

(54) PRESSURE TEST CONTAINMENT VESSEL

(71) Applicant: FMC Technologies, Inc., Houston, TX (US)

(72) Inventors: Michael L. Mann, Houston, TX (US); Robert P. Matson, Cypress, TX (US)

(73) Assignee: FMC Technologies, Inc., Houston, TX (US)

( * ) Notice: Subject to any disclaimer, the term of this patent is extended or adjusted under 35 U.S.C. 154(b) by 467 days.

(21) Appl. No.: 13/886,947

(22) Filed: May 3, 2013

(65) Prior Publication Data
US 2014/0326050 A1 Nov. 6, 2014

(51) Int. Cl.
G01N 3/12 (2006.01)
G01M 3/02 (2006.01)
G01M 3/04 (2006.01)
G01M 3/06 (2006.01)
G01M 3/26 (2006.01)
G01M 3/32 (2006.01)

(52) U.S. Cl.
CPC ............... G01N 3/12 (2013.01); G01M 3/02 (2013.01); G01M 3/04 (2013.01); G01M 3/06 (2013.01); G01M 3/26 (2013.01); G01M 3/329 (2013.01)

(58) Field of Classification Search
CPC ............ G01M 3/02; G01M 3/04; G01M 3/06; G01M 3/26; G01M 3/329; G01M 3/2815; G01M 3/2807; G01M 3/2853; G01N 3/12; G01N 2203/0274; G01N 2203/0042; G01N 2203/0067
See application file for complete search history.

(56) References Cited

U.S. PATENT DOCUMENTS

| 3,595,066 | A | | 7/1971 | Yamamoto | |
|---|---|---|---|---|---|
| 3,955,402 | A | * | 5/1976 | Harvill | G01N 3/12 73/37 |
| 3,958,448 | A | * | 5/1976 | Willis | G01N 3/12 73/37 |
| 4,089,208 | A | | 5/1978 | Franks et al. | |

(Continued)

FOREIGN PATENT DOCUMENTS

CN 201955205 U 8/2011
CN 202305339 U 7/2012
(Continued)

OTHER PUBLICATIONS

Extended European Search Report issued in corresponding European Application No. EP14167040.6; Dated Mar. 12, 2015 (12 pages).

(Continued)

Primary Examiner — Freddie Kirkland, III
(74) Attorney, Agent, or Firm — Osha Liang LLP

(57) ABSTRACT

A portable containment vessel to perform a pressure test to a test specimen includes a base skid, a ballistic outer enclosure connected to the base skid and comprising a plurality of walls, a door, and a lock to maintain the door in a closed position, a sample tray configured to support the test specimen, wherein the sample tray is operable through a doorway of the ballistic outer enclosure between a retracted position and an extended position, a containment fluid to surround the test specimen while a pressurized test fluid is applied to the test specimen, and a sensor to indicate a failure of the pressure test.

21 Claims, 2 Drawing Sheets

(56) References Cited

U.S. PATENT DOCUMENTS

| | | | |
|---|---|---|---|
| 4,345,458 A * | 8/1982 | Kosaka | F17C 13/002 73/37.5 |
| 4,523,454 A | 6/1985 | Sharp | |
| 4,977,418 A * | 12/1990 | Canty | B01J 3/004 348/81 |
| 5,057,171 A | 10/1991 | Horner et al. | |
| 5,123,278 A * | 6/1992 | McKittrick | G01N 3/12 73/49.3 |
| 5,220,824 A * | 6/1993 | Shelleman | G01N 3/12 374/57 |
| 5,834,630 A | 11/1998 | Fukushi | |
| 6,082,182 A | 7/2000 | Fierro et al. | |
| 6,253,599 B1 * | 7/2001 | Chang | G01N 3/12 285/323 |
| 6,619,104 B1 * | 9/2003 | Yeh | G01N 3/12 73/49.1 |
| 7,647,819 B2 * | 1/2010 | Garcia Gomez | G01N 3/12 73/49.1 |
| 8,146,428 B2 * | 4/2012 | Lavergne | G01N 3/12 73/583 |
| 8,453,515 B2 * | 6/2013 | Wang | G01N 3/36 73/807 |
| 2003/0046981 A1 | 3/2003 | Bennett et al. | |
| 2006/0102015 A1 | 5/2006 | Baker et al. | |
| 2008/0264632 A1 | 10/2008 | David et al. | |
| 2010/0037710 A1 | 2/2010 | Lavergne | |

FOREIGN PATENT DOCUMENTS

| | | |
|---|---|---|
| GB | 840294 A | 7/1960 |
| JP | 5642121 A | 4/1981 |

OTHER PUBLICATIONS

Shelleman, D. L., et al., "High Temperature Tube Burst Test Apparatus", Journal of Testing and Evaluation, American Society for Testing and Materials, Philadelphia, U.S., vol. 20, No. 4, Jul. 1, 1992, XP000321477, pp. 275-284.

Examination Report issued in Australian Application No. 2014202354; Dated Sep. 3, 2015 (3 pages).

Search Report issued in corresponding Singaporean Application No. 10201402022T dated Jun. 3, 2015 (9 pages).

Written Opinion issued in corresponding Singaporean Application No. 10201402022T dated Jun. 18, 2015 (15 pages).

Written Opinion issued in corresponding Singaporean Application No. 10201402022T dated Jan. 12, 2016 (13 pages).

Examination Report issued in Australian Application No. 2014202354; Dated Dec. 15, 2015 (3 pages).

\* cited by examiner

PRESSURE TEST CONTAINMENT VESSEL

BACKGROUND OF THE DISCLOSURE

Field of the Disclosure

The present disclosure relates to methods and apparatuses to contain test samples undergoing pressure testing operations. More particularly, methods and apparatuses disclosed herein relate to portable vessels to contain test specimens being tested with liquids and gasses at elevated pressures.

Description of the Related Art

Oilfield operations, like those of other industries, are increasingly carried out in varied and remote locations throughout the world. As a result, the ability to carry out tasks such as component testing, maintenance, and repair at the varied remote locations is highly desirable. One such task is the component pressure test.

Oilfield components are typically placed in high-temperature (e.g., in excess of 200° C.), high-pressure (e.g., in excess of 135 MPa, or 20 ksi), and high-shock (e.g., in excess of 20 g, or 196 m/s$^2$, of acceleration) service. Oilfield components and tools are frequently submerged in subterranean wells drilled several kilometers beneath the earth's surface (or sea floor) where all three extremes (temperature, pressure, and shock) exist simultaneously. Often, such components include complex electronics, hydraulic regulation and distribution systems, and sensors that must be hydraulically or pneumatically isolated from their surroundings. Additionally, equipment used at the surface of such well locations, while not experiencing the same environments as their downhole counterparts, often interact with the downhole components such that their hydraulic and/or pneumatic integrity must also be tested and maintained if operations are to succeed.

Therefore, it is common for such components to be thoroughly proof tested to have their hydraulic and/or pneumatic integrity verified following assembly, maintenance, and repair, but prior to being shipped from a regional facility to the specific location where they are to be placed into service. Such integrity tests typically include connecting a test volume of a component specimen to be tested to a high-pressure testing system and surrounding or encapsulating the specimen in some form of containment vessel in the event that the component specimen experiences a catastrophic failure during the test. At such elevated pressures, tests performed with compressible fluids (e.g., gasses) may produce catastrophic results in the event of such a failure as the compressible nature of the fluid allows the build-up of significant potential energy (in the form of the compressed gas) that may experience an explosive kinetic release should the hydraulic and/or pneumatic integrity of the component specimen fail the pressure test.

As a result, elevated pressure tests are often performed in strictly controlled environments (e.g., in shielded and reinforced bunkers or subterranean facilities) such that should a component specimen exhibit a failure, damage to the surrounding structures, assets, and people may be reduced or prevented. However, as should be understood by those having ordinary skill, various components that are tested and verified at the regional facility may become damaged or may require additional service after they been delivered to a remote location. Such supplemental tests may be necessary because the component may require modification or repair before they are placed into service or, in certain circumstances, they have failed in service and must be repaired on-site quickly before a replacement can be obtained. With operating costs aboard many offshore rigs exceeding several hundred thousand U.S. dollars per day, the potential economic loss associated to shipping a mission-critical component back to the regional facility for repair and re-verification can be significant. With the potential economic cost of a component failure being so significant, operating companies would consider a portable, remote location-based pressure testing and verification solution to be highly desirable.

SUMMARY OF THE CLAIMED SUBJECT MATTER

In one aspect, the present disclosure relates to a portable containment vessel to perform a pressure test to a test specimen, the portable containment vessel including a base skid, a ballistic outer enclosure connected to the base skid and including a plurality of walls, a door, and a lock to maintain the door in a closed position, a sample tray configured to support the test specimen, wherein the sample tray is operable through a doorway of the ballistic outer enclosure between a retracted position and an extended position, a containment fluid to surround the test specimen while a pressurized fluid is applied to the test specimen, and a sensor to indicate a failure of the pressure test.

In another aspect, the present disclosure relates to a method to test the internal pressure integrity of a test specimen including positioning the test specimen inside a ballistic outer enclosure, connecting the test specimen to a test fluid supply, sealing the test specimen within the ballistic enclosure, filling the ballistic enclosure with a containment fluid, increasing a pressure of the test fluid supply to a desired test pressure, and monitoring the test specimen to determine its internal pressure integrity.

In another aspect, the present disclosure relates to a containment vessel to perform a pressure test to a test specimen, the containment vessel including a base skid, a ballistic outer enclosure connected to the base skid, at least one fluid-tight membrane positioned within the ballistic outer enclosure, a manifold assembly configured to selectively apply a pressurized test fluid to the test specimen, a containment fluid to surround the test specimen within the ballistic outer enclosure and at least one fluid-tight membrane while the pressurized test fluid is applied to the test specimen, and a sensor to indicate a failure of the pressure test.

BRIEF DESCRIPTION OF DRAWINGS

Features of the present disclosure will become more apparent from the following description in conjunction with the accompanying drawings.

DETAILED DESCRIPTION

Selected embodiments disclosed herein relate to assemblies and methods to contain test specimens during a pressure test using a portable containment vessel. As such, selected embodiments disclosed herein relate to a ballistic outer enclosure having a plurality of walls, a door, and a lock attached to a moveable base skid. Additionally, selected embodiments further relate to a sample tray operable through a doorway of the ballistic enclosure between an extended position and a retracted position, wherein the sample tray is configured to support the test specimen. Additionally, selected embodiments further relate to a manifold assembly to apply a pressurized test fluid to the test specimen, a containment fluid to surround the test specimen while pressurized, and a sensor to indicate escape of the pressurized test fluid from the test specimen. Additionally still, selected embodiments further relate to a fluid-tight membrane positioned within the ballistic outer enclosure to retain the containment fluid.

Figure 1:
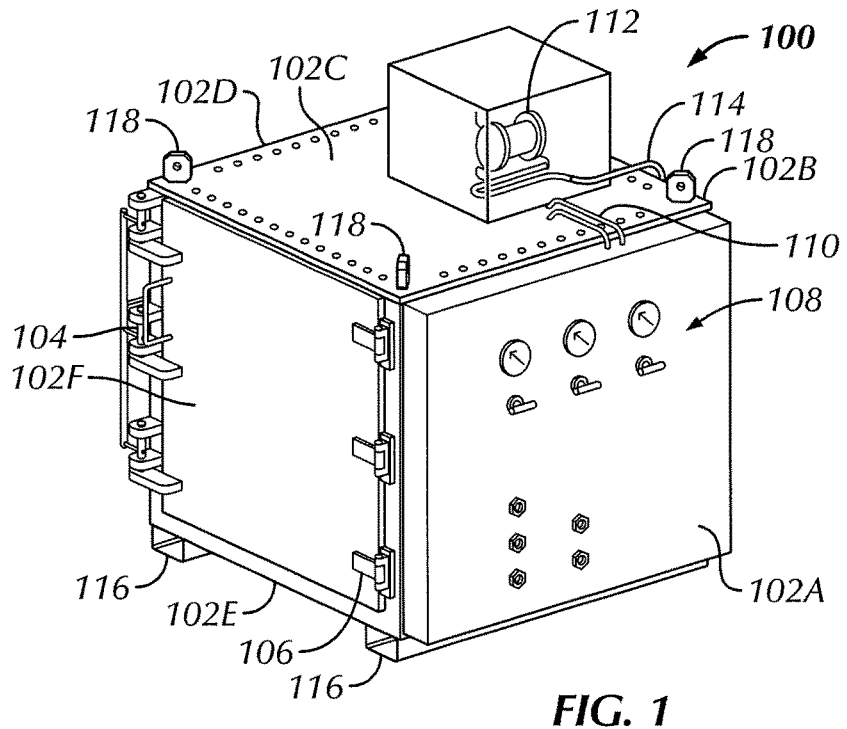
FIG. 1 is an isometric-view drawing of a containment vessel shown with its door in a closed position in accordance with one or more embodiments of the present disclosure.

Referring initially to FIG. 1, a portable containment vessel 100 in accordance with selected embodiments of the present disclosure is shown. Portable containment vessel 100 includes an ballistic outer enclosure 102 having a plurality of walls 102A, 102B, 102C, 102D, 102E, and a door 102F operable between a closed position (shown) and one or more open positions (e.g., FIGS. 2 and 3). A lock mechanism 104 is shown to secure door 102F to a location adjacent to left side wall 102D, and a hinge apparatus 106 allows door 102F to rotate between closed and open positions. While door 102F is shown in FIGS. 1-3 as a hinge-type door rotating about an axis of hinges 106, it should be understood by those having ordinary skill that door 102F may be any type door known in the art including, but not limited to, sliding doors, roll-up doors, folding doors, and/or other types of rotating (hinged or otherwise) doors.

With door 102F of containment vessel 100 closed, a manifold assembly 108 may be used to supply high-pressure test fluid through high pressure lines 110 to a test specimen (e.g., 128 of FIG. 2) contained within walls 102A-102E and door 102F of containment vessel 100. As would be understood by those having ordinary skill, manifold assembly 108 may include any combination of gauges and valves known in the art to direct the high-pressure test fluid to a volume to be tested within test specimen (e.g., 128 of FIG. 2) contained within vessel 100.

Additionally, containment vessel 100 may also include a low-pressure fill pump 112 to direct a containment fluid through fluid supply line 114 and into the volume of containment vessel generally defined by walls 102A-102E and door 102F. Finally, as shown in the embodiment disclosed in FIG. 1, containment vessel 100 may additionally include handling features in the form of forklift legs 116 and lifting pad-eyes 118 to facilitate the lifting, movement, and placement of containment vessel 100 to a desired location by an overhead crane, a forklift, or other material-handling machine. Alternatively still, containment vessel 100 may include one or more casters or wheels (not shown) to assist in maneuvering it from one location to another without the assistance of a material-handling machine. As such, a person having ordinary skill in the art of material handling and/or oilfield technology would understand the term "skid" to appropriately describe construction and arrangement of handling features (e.g., forklift legs 116 and lifting pad-eyes 118) integrated with containment vessel 100 in that the term is frequently used to describe a piece of equipment having a unitized structure that is configured for easy manipulation and movement by commonly-found industrial handling machines.

Figure 2:
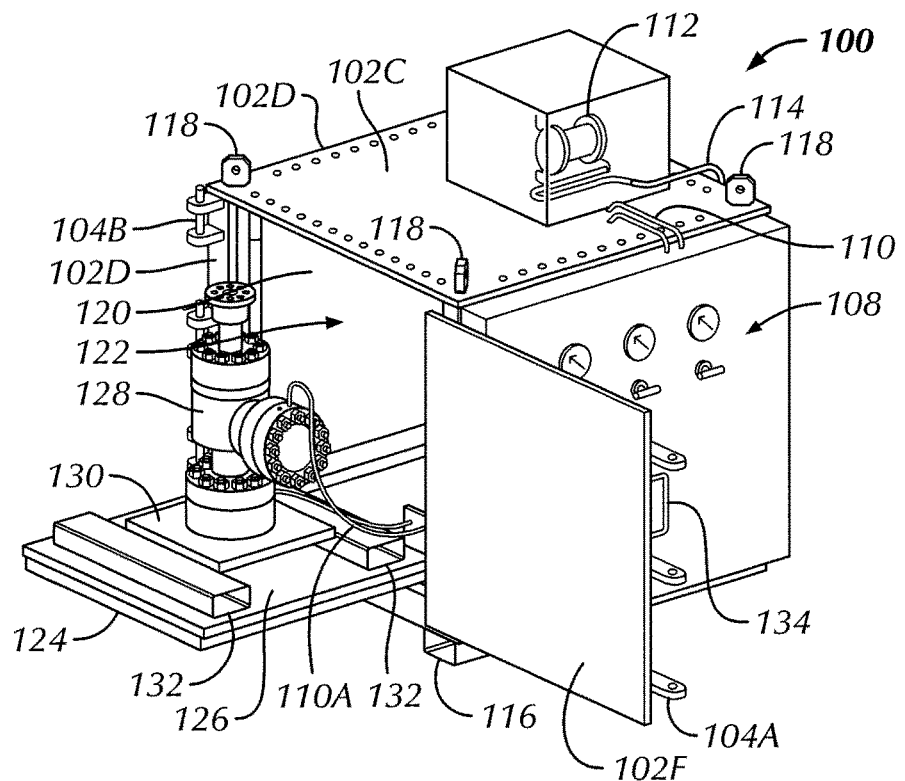
FIG. 2 is an isometric-view drawing of the containment vessel of FIG. 1 shown with its door in a fully-open position in accordance with one or more embodiments of the present disclosure.
Figure 3:
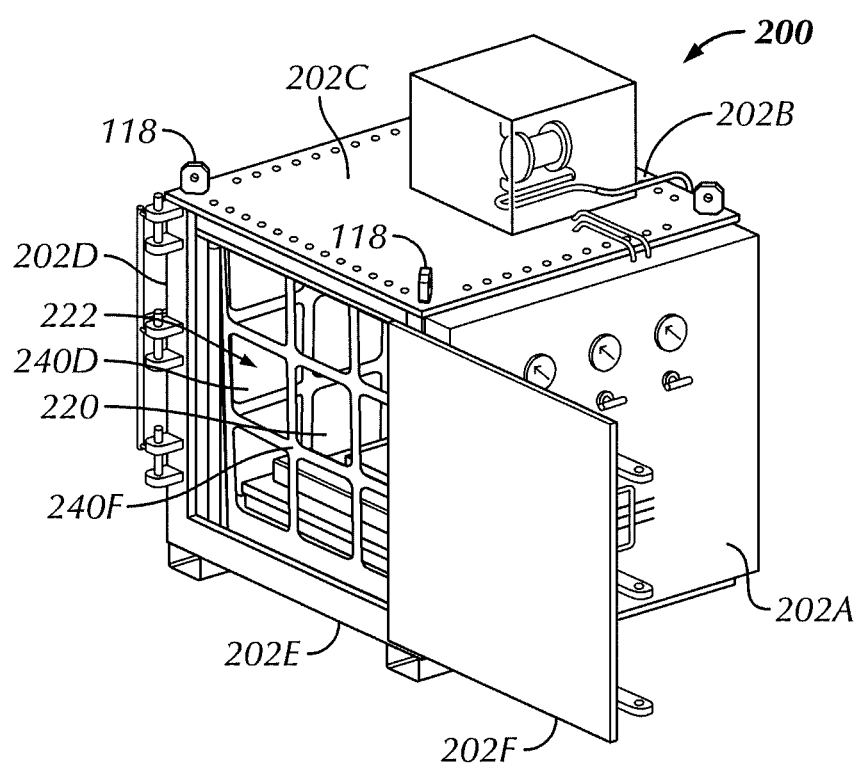
FIG. 3 is an isometric-view drawing of a containment vessel having a water-tight membrane in accordance with one or more embodiments of the present disclosure.

Referring now to FIG. 2, containment vessel 100 of FIG. 1 is shown with door 102F in a fully-open position, allowing full access to an interior volume 120 through a doorway 122 defined generally by walls 102A-102E such that when closed, doorway 122 is blocked by door 102F (as shown in FIG. 1). A sample tray 124, shown in FIG. 2 in a fully extended position, provides a work surface 126 upon which a test specimen 128 may be placed prior to retracting sample tray 124 into interior volume 120 of containment vessel 100.

As shown, sample tray 124 and work surface 126 may be fully retracted within, or fully extended from interior volume 120 of containment vessel. In selected embodiments, sample tray 124 may retract and extend into and from interior volume 120 upon roller bearings, friction slides, or any other linear or non-linear material handling mechanism known to those having ordinary skill in the art. Additionally, movement of sample tray 124 may be displaced manually (e.g., by an operator) between retracted and extended positions or with the assistance of powered mechanisms (not shown) including, but not limited to, hydraulic rams, pneumatic rams, electric motors, linear thrusters, and the like. In selected embodiments, sample tray 124 may not fully extend from interior volume 120 of containment vessel 100, and in other embodiments, sample tray 124 may extend beyond "full" extension from interior volume 120.

With sample tray 124 extended as shown in FIG. 2, a crane, forklift, or other lifting or material-handling machine may have full access (overhead, from the front, and from one or more sides) to work surface 126 such that test specimen 128 may be positioned thereupon without interference from walls 102A-102E, door 102F, or any other component of containment vessel 100. As shown in FIG. 2, test specimen 128 may comprise a base plate 130 and one or more forklift legs 132, to facilitate loading of test specimen 128 onto work surface 126. With test specimen 128 positioned upon work surface 126 of sample tray 124, an operator is able to connect internal high pressure lines 110A that are in fluid communication with external high pressure lines 110 and manifold assembly 108 to pressure test fittings (not shown) on test specimen. As would be understood by those having ordinary skill, pressure test fittings allow communication of test fluid from manifold assembly 108 to communicate with and pressurize a test volume (not shown) within test specimen 128 through high pressure lines 110 and 110A.

With test specimen 128 positioned upon work surface 126 of sample tray 124 and high pressure lines 110A connected to the satisfaction of the operator overseeing the pressure test of specimen 128, sample tray 124 may be retracted (either manually or with mechanical assistance) back into interior volume 120 of containment vessel 100 so that door 102F may be closed. As shown, door 102F may include a handle 134 and a first component 104A of lock mechanism 104 (FIG. 1) to engage a second component 104B of lock mechanism 104 proximal to side wall 102D of outer enclosure 102. With door 102F closed behind retracted sample tray 124, components 104A and 104B of lock 104 may be engaged to securely enclose test specimen 128 within interior volume 120 of containment vessel 100.

With test specimen 128 connected to high pressure lines 110, 110A and door 102F secured and locked by mechanism 104, internal volume 120 of containment vessel 100 may be filled with a containment fluid using pump 112 and supply line 114. Alternatively, should no pump 112 be installed to containment vessel 100, containment fluid may be manually added to interior volume of closed containment vessel 100 through a port (not shown) located on the exterior of ballistic outer enclosure 102.

As used herein, the term "ballistic" in reference to outer enclosure 102 refers to the ability of walls (102A-102E) and door 102F of enclosure 102 to retard, retain, or otherwise constrain an accelerated mass from within enclosure 102 that might otherwise tend to penetrate outer enclosure 102, potentially causing damage to nearby equipment, workers, or the containment vessel 100 itself. As would be understood by those having ordinary skill, the amount of ballistic ability desired for walls 102A-102E and door 102F of outer enclosure 102 may depend on the type, configuration, and size of test specimen 128 to be tested as well as the type and pressure of the test fluid to be applied by manifold assembly 108 and high pressure lines 110.

For example, an incompressible test fluid (e.g., water, glycol, drilling mud, etc.) applied to an internal test volume of test specimen 128 may require less ballistic protection from outer enclosure 102 than a compressible test fluid (e.g., air, nitrogen gas, etc.) applied to the same test specimen 128 being tested at the same test pressure. As known to those skilled in the art, pressurized compressible fluids (e.g., gasses) exhibit much more rapid expansion (i.e., release of potential energy through kinetic energy) upon their release than do their incompressible counterparts. While those having ordinary skill will appreciate that it may be "safer" to only pressure test a specimen (e.g., test specimen 128) using an incompressible medium, the design and function of the specimen (e.g., those having internal electronic components) may require a "dry" test be performed by an inert or otherwise non-reactive medium such as compressible nitrogen gas.

Additionally, depending on the amount of test pressure to be applied to test fluid through lines 110 connected to test volume of test specimen 128, the thickness, material, geometry, and construction of walls 102A-102E and door 102F may be varied to maximize the amount of kinetic energy containable within outer enclosure 102 when used in conjunction with a given containment fluid at a specified test pressure. For example, walls 102A-102E and door 102F may be constructed of various forms of steel (e.g., cast, forged, cold worked, etc.), aluminum, tungsten, Kevlar, carbon-fiber composite, or any other material known in the art.

Additionally the walls 102A-102E and door 102F of outer enclosure 102 may be constructed as single-thickness "plates" of a single material or as a multi-laminated "sandwich" of one or more different materials to increase ballistic strength and/or reduce the overall weight of containment vessel 100. For example, tests have shown that a ballistic wall panel (e.g. 102A-102F) constructed of ten plies of 2 mm steel may have a increased ballistic resistance relative to a ballistic wall panel constructed of a single 2 cm steel panel for a given test specimen 128 at a specified test pressure. Moreover, constructing such a laminated panel with layers of carbon-fiber composite or Kevlar interleaved between adjacent plies of steel may have the benefit of greatly increasing ballistic resistance while only minimally increasing the overall weight and/or thickness of the panel.

In alternative embodiments, walls 102A-102E and door 102F may be constructed of lightweight, relatively inexpensive and easily replaceable "sacrificial" materials (e.g., carbon fiber composite or Kevlar) held into place by a high strength rigid space frame to contain releases of potential energy from test specimen 128 within interior volume 120. Thus, in the event of a sudden pressure release from test specimen 128, only the affected or otherwise damaged wall panels (102A-102F) may be replaced rather than requiring shipping and repair of the entire containment vessel 100 assembly. Alternatively still, panels of each wall 102A-102E and door 102F may be constructed from different materials should anisotropic containment of a particular test specimen 128 be desired or otherwise advantageous for a particular test. Alternatively still, outer enclosure 102 may be constructed such that containment vessel assembly 100 can be assembled surrounding a particular test specimen 128 while in use so that an in-situ pressure test of specimen 128 may be performed.

Referring now to FIG. 3, a containment vessel 200 in accordance with one or more alternative embodiments of the present disclosure is shown. Containment vessel 200 is similar to containment vessel 100 of FIGS. 1-2, with the exception that containment vessel 200 additionally includes one or more fluid-tight membranes 240D, 240F separating walls 202A-202E and door 202F of outer enclosure 202 from interior volume 220 of containment vessel 200. While only fluid-tight membranes 240D and 240F corresponding to wall 202D and door 202F are visible in FIG. 3, it should be understood that additional fluid-tight membranes (i.e., 240A, 240B, 240C, and 240E) corresponding to walls 202A, 202B, 202C, and 202E may also be present.

As would be understood by those having ordinary skill in the art, fluid-tight membranes (referred to as 240, generally) may comprise any substantially flexible material capable of containing fluids within interior volume 220 of containment vessel 200 including, but not limited to PVC, silicone, polyethylene, and/or other similar elastomers and polymers. Additionally, depending on configuration and preference, fluid tight-membranes 240 may be located adjacent to one or more walls 202A-202E, door 202F, or any combination thereof. As such, fluid-tight membranes may be used to isolate or protect interior components (e.g., manifold assembly 108 of FIGS. 1-2) from containment fluids, or may be used to retain containment fluids within interior volume 220 with door 202F partially or fully open (as shown in FIG. 3).

In selected embodiments, fluid-tight membranes may be constructed as transparent, semi-transparent, partially opaque, or fully opaque so that the internal volume 220 of containment vessel 200 may be viewable through membranes 240, if desired. Thus, an operator may enclose a test specimen (e.g., 128) within interior volume 220 of vessel 200, secure fluid-tight membranes 240 closed, and observe and monitor test specimen 128 during the early phase of a pressure test to determine if leaks of test fluid are occurring at such low pressures. When pressure of test fluid is increased, the operator may then close and lock door 202F to engage the full ballistic integrity of outer enclosure 202.

Additionally, in selected embodiments, fluid-tight membrane 240F adjacent to doorway 222 of containment vessel 200 may be constructed in a retractable or otherwise quickly and easily removable (e.g., through automated and computer controlled cylinders, servos, etc.) configuration. For example, in selected embodiments, fluid tight membrane 240F may be retractable into a recess or pocket located adjacent to a lower, upper, right, or left side end of doorway 222. In selected embodiments, one or more mechanical fasteners may assist in maintaining a fluid-tight seal between membrane 240F and upper, lower, right, and/or left side ends of doorway 222. As would be understood by those having ordinary skill, such fasteners may include, but should not be limited to, magnets, hooks, snaps, zippers, and the like. In selected alternative embodiments, operation (e.g., retraction and extension) of fluid-tight membranes may be automated by one or more mechanical devices.

Referring generally to FIGS. 1-3 together, the use of containment vessels 100 and 200 may now be described in detail. In selected embodiments, containment vessels 100, 200 are desired to be small and portable relative to comparable vessels located in manufacturing, testing, and repair facilities. As such, containment vessels 100, 200 may be designed, constructed, and deployed throughout the world to locations that are far more remote and/or numerous than otherwise serviceable with a traditional, more permanent testing structure. Once so deployed, site operators are able to use conventional material handling devices including, but not limited to fork lifts, overhead cranes, and the like, to easily load and position the portable containment vessel (100 or 200) to a desired location. In certain installations, containment vessels 100, 200 may be located directly upon a remote drilling rig, a drillship, or any other operations site where on-site pressure testing and integrity validation tests are desirable.

Upon location at the worksite, the locking mechanism 104 may be unlatched, the door 102F, 202F opened, and sample tray 124 extended from the internal volume 120, 220 of the outer enclosure 102, 202 so that a test specimen (e.g., 128 of FIG. 2) may be placed upon work surface 126. At this time, an operator may proceed to connect internal high-pressure fluid lines 110A to test specimen 128 such that the testing fluid will be in communication with a volume to be tested within test specimen 128. Once connected, sample tray 124 may be retracted either manually or through an aforementioned method of mechanical assistance, fluid-tight membrane 240F (if present) blocking doorway 122, 222 may be engaged, and door 102F, 202F closed and locking mechanism 104 engaged.

Once door 102F, 202F of containment vessel 100, 200 is locked, a containment fluid may be pumped in (using low-pressure fill pump 112 and fluid supply line 114) or otherwise poured into the internal volume 120, 220 surrounding test specimen 128 and bounded by walls 102A-102F, 202A-202F and/or fluid-tight membranes 240A-240F (if present) until a desired amount of containment fluid surrounds test specimen 128. In one or more alternative embodiments, the containment fluid may comprise a gas (e.g., air) that may either be pumped into or may already be present within containment vessel 100, 200. Once submerged in or surrounded by containment fluid, a pressurized test fluid may be supplied to test volume of test specimen 128 through high-pressure lines 110, 110A and manifold assembly 108 at a selected pressure desired for the pressure test.

Alternatively, in embodiments where fluid-tight membranes 240 are present, the operator may fill the internal volume 220 with containment fluid prior to closing and locking door 202F, so that test fluid may be supplied to test volume of test specimen 128 at an initial, reduced pressure to ensure that connections between test specimen 128, lines 110, 110A, and manifold assembly 108 have been correctly made. Once connection integrity of high pressure lines 110, 110A and manifold assembly 108 to test specimen 128 has been confirmed, the operator may then close and lock door 202F before proceeding with pressure testing at elevated pressures. Additionally, in selected embodiments, testing operations may be performed autonomously using a control system so that the test specimen 128 and high pressure lines 110, 110A are not disturbed during the testing operations.

As would be understood by those having ordinary skill in the art, the containment fluid used with embodiments disclosed herein may comprise any fluid (i.e., liquid, gas, gel, or a combination thereof) exhibiting ballistic qualities in reducing the kinetic energy of masses in the aftermath of a sudden (e.g., explosive) release of potential energy. As such, various fluid characteristics including, but not limited to fluid compressibility, density (or specific gravity), corrosivity, pH, surface tension, viscosity, and the like may be specified in determining a desirable candidate for containment fluid. However, as containment vessels 100 and 200 are capable of being used at various remote locations, the containment fluid may be selected from fluids readily available including, but not limited to water, drilling fluid, ethylene glycol, silicone fluid, sand slurries, oil, and/or non-combustive gasses like air, helium, and nitrogen.

Additionally, as would be understood by those having ordinary skill in the art, the test fluid used with embodiments disclosed herein may comprise any fluid (i.e., liquid, gas, gel, or combination thereof) known to be useful in performing pressure tests to test volumes. Similarly to containment fluid described above, test fluid may be selected based upon a variety of fluid characteristics including, but not limited to compressibility, density, corrosivity, pH, surface tension, viscosity, and may be selected from fluids readably available at the test site. As would be understood by those having ordinary skill, test fluids may be selected and used to test specimens (e.g., 128) up to and in excess of 135 MPa (20 ksi) for compressible testing fluids and up to and in excess of 200 MPa (30 ksi) for incompressible testing fluids.

Additionally, in selected embodiments, candidates for containment and test fluids may be evaluated and selected based upon their abilities to indicate the presence of leaks or other test volume failures within the internal volume 120, 220 defined by outer enclosures 102, 202 and membranes 240 (if present). In particular, by selecting a relatively transparent or translucent liquid for containment fluid and a gas for test fluid, bubbles will be apparent and observable in the containment fluid, should a leak or other disruption in hydraulic integrity of test specimen 128 occur. Alternatively, should a liquid be desired for test fluid, a dye may be included with test fluid such that a color change in containment fluid would be visible should test fluid leak from test specimen 128. Alternatively still, an operator may closely monitor a gauge (not shown) of manifold assembly 108, so that an internal failure (i.e., a failure where the leaking test fluid is contained within test specimen 128) of test volume may be detected by observing a sudden drop in pressure of the test fluid.

Additionally, one or more sensing devices including, but not limited to, flow sensors, transducers, and gas leak detectors, (not shown) may be installed within internal volume 120, 220 of containment vessels 100, 200 to detect the invasion of test fluid (and therefore the failure of the pressure test) into the containment fluid located within internal volume 120, 220. For example, for a test fluid comprising a gas, a gas detector or sensor designed to detect that particular gas may be installed to the internal volume 120, 220 to send a signal should presence of the test fluid be detected within the containment fluid. Alternatively still, one or more camera devices may be installed within internal volume 120, 220 of containment vessels 100, 200 so that an operator may view the test specimen 128 as the test is being performed. Finally, in order to accommodate circumstances where a test specimen (e.g., 128) is to be placed into high-temperature and high-pressure (HTHP) service, one or more heating elements (not shown) may be placed within internal volume 120, 220 of containment vessels 100, 200 to allow a HTHP test to be performed.

Advantageously, embodiments disclosed herein allow a test specimen to be safely pressure tested in remote locations, locations that can be several travel days removed from the closest traditional pressure test facility. As such, embodiments disclosed herein allow operators to safely perform verification testing on-site (and with various combinations of test and containment fluids) thereby allowing various operations such as modification, assembly, and refurbishment of components shortly before, during, and after they are deployed to remote or field locations. As such, defective components may be identified and repaired locally before they are placed in service, as opposed to after when such repair would be more inconvenient, time consuming, expensive, and difficult.

Advantageously still, embodiments disclosed herein allow for the application of different mediums (e.g., water and/or Nitrogen gas) to an inner volume of a test article without having to change or disturb the supply and/or vent high pressure lines to the test article between testing operations. Additionally, embodiments disclosed herein may allow an automatic sequence of testing the specimen first with a non-compressible test fluid at a first pressure to verify pressure integrity, followed by the filling of the ballistic enclosure with a containment fluid medium and a subsequent testing of test article with a compressible (e.g., a gas) test fluid at a second pressure. In selected embodiments, the first pressure test may verify pressure integrity through detection of a stable pressure within the test specimen (e.g., monitored with a pressure sensor) while the second pressure test may verify sealing integrity through the observance of bubbles (using a camera or other sensor) escaping the test specimen into the containment fluid. In selected embodiments, the apparatus may be automated such that the test specimen may be tested without requiring disturbance of the test specimen or high pressure lines between subsequent test operations.

While the disclosure has been presented with respect to a limited number of embodiments, those skilled in the art, having benefit of this disclosure, will appreciate that other embodiments may be devised which do not depart from the scope of the present disclosure. Accordingly, the scope of the invention should be limited only by the attached claims, although additional combinations of independent and dependent claims beyond those specifically recited below are fully contemplated by the inventors and supported by the specification above.

What is claimed is:

1. A portable containment vessel to perform a pressure test to a test specimen, the portable containment vessel comprising:
   a base skid;
   a ballistic outer enclosure connected to the base skid and comprising a plurality of walls, a door, and a lock to maintain the door in a closed position;
   a sample tray configured to support the test specimen, wherein the sample tray is operable through a doorway of the ballistic outer enclosure between a retracted position and an extended position;
   a containment fluid to surround the test specimen while a pressurized fluid is applied to the test specimen;
   a sensor to indicate escape of the pressurized fluid from the test specimen; and
   at least one fluid tight polymeric membrane positioned within the ballistic outer enclosure, wherein the at least one fluid tight polymeric membrane allows the test specimen to be monitored while the door of the ballistic outer enclosure is open.

2. The portable containment vessel of claim 1, wherein the at least one fluid tight polymeric membrane is positioned adjacent to the door of the ballistic outer enclosure, and is retractable to allow access to an interior volume when the door is in an open position.

3. The portable containment vessel of claim 1, further comprising a manifold assembly to selectively apply the pressurized test fluid to the test specimen.

4. The portable containment vessel of claim 1, wherein the sensor comprises a camera.

5. The portable containment vessel of claim 1, wherein the sensor comprises a pressure gauge.

6. The portable containment vessel of claim 1, wherein the sensor is configured to detect a presence of the test fluid in the containment liquid.

7. The portable containment vessel of claim 1, wherein the containment fluid comprises water.

8. The portable containment vessel of claim 1, wherein the containment fluid comprises drilling mud.

9. The portable containment vessel of claim 1, wherein the containment fluid comprises a gas.

10. The portable containment vessel of claim 1, further comprising a pump to supply the containment fluid to an interior volume of the ballistic outer enclosure.

11. The portable containment vessel of claim 1, further comprising a heater to increase the temperature of the test specimen.

12. A method to test the internal pressure integrity of a test specimen, the method comprising:
    positioning the test specimen inside a ballistic outer enclosure;
    connecting the test specimen to a test fluid supply;
    sealing the test specimen within the ballistic enclosure with at least one fluid-tight polymeric membrane;
    filling the ballistic enclosure with a containment fluid;
    increasing a pressure of the test fluid supply to a desired test pressure; and
    monitoring the test specimen through the fluid-tight polymeric membrane while a door of the ballistic outer enclosure is open to determine its internal pressure integrity.

13. The method of claim 12, further comprising positioning the test specimen inside the outer enclosure with an extendable sample tray.

14. The method of claim 12, wherein the fluid-tight polymeric membrane is transparent, semi-transparent, or partially opaque.

15. The method of claim 12, further comprising monitoring the test specimen with a camera.

16. The method of claim 12, further comprising monitoring the test specimen with a sensor configured to detect the presence of the test fluid in the containment fluid.

17. The method of claim 12, further comprising heating the test specimen.

18. The method of claim 12, further comprising:
    testing the test specimen at a first test pressure using a first test fluid supply and a first containment fluid; and
    testing the test specimen at a second test pressure using a second test fluid supply and a second containment fluid.

19. A containment vessel to perform a pressure test to a test specimen, the containment vessel comprising:
    a base skid;
    a ballistic outer enclosure connected to the base skid;
    at least one fluid-tight polymeric membrane positioned within the ballistic outer enclosure, wherein the at least one fluid tight polymeric membrane allows the test specimen to be monitored while a door of the ballistic outer enclosure is open;
    a manifold assembly configured to selectively apply a pressurized test fluid to the test specimen;
    a containment fluid to surround the test specimen, the test specimen within the ballistic outer enclosure and the at least one fluid-tight polymeric membrane while the pressurized test fluid is applied to the test specimen; and a sensor to indicate escape of the pressurized test fluid from the test specimen.

20. The containment vessel of claim 19, wherein a first of the at least one fluid tight polymeric membrane is positioned adjacent to the door of the ballistic outer enclosure and is retractable to allow access to an interior volume when the first of the at least one fluid tight polymeric membrane is in an open position.

21. The containment vessel of claim 19, further comprising a sample tray to support the test specimen, wherein the sample tray is operable through a doorway of the ballistic outer enclosure between a retracted position and an extended position.

* * * * *